United States Patent [19]

Jaedicke et al.

[11] 4,335,047
[45] Jun. 15, 1982

[54] PREPARATION OF CYCLIC ACETALS OF TRANS-4-CHLORO-3-METHYL-BUT-2-EN-1-AL, AND PREPARATION OF TRANS-3-METHYL-BUT-2-ENE-1,4-DIAL-1-MONOACETALS

[75] Inventors: Hagen Jaedicke, Ludwigshafen; Joachim Paust, Neuhofen, both of Fed. Rep. of Germany

[73] Assignee: BASF Aktiengesellschaft, Ludwigshafen, Fed. Rep. of Germany

[21] Appl. No.: 138,411

[22] Filed: Apr. 8, 1980

[30] Foreign Application Priority Data

Apr. 28, 1979 [DE] Fed. Rep. of Germany ....... 2917413

[51] Int. Cl.$^3$ ............................................. C07D 319/04
[52] U.S. Cl. ..................................... 549/369; 549/375
[58] Field of Search ...................................... 260/340.7

[56] References Cited

U.S. PATENT DOCUMENTS

| | | | |
|---|---|---|---|
| 3,840,559 | 10/1974 | Hoffmann | 260/340.7 |
| 4,044,026 | 8/1977 | Paust | 260/340.7 |
| 4,192,806 | 3/1980 | Paust et al. | 260/340.7 |
| 4,256,643 | 3/1981 | Jaedicke et al. | 260/340.7 |

FOREIGN PATENT DOCUMENTS 2357752 5/1975 Fed. Rep. of Germany ... 260/340.7

*Primary Examiner*—Ethel G. Love
*Attorney, Agent, or Firm*—Oblon, Fisher, Spivak, McClelland & Maier

[57] ABSTRACT

A process for the preparation of 6-membered cyclic acetals of trans-4-chloro-3-methyl-but-2-en-1-al by reacting the corresponding acetals of 3-methyl-but-2-en-1-al (prenal), in a halohydrocarbon, with sulfuryl chloride and for their subsequent oxidation to trans-3-methyl-but-2-ene-1,4-dial-1-monoacetals (3-methyl-fumarodialdehyde-1-monoacetals). The trans-3-methyl-but-2-ene-1,4-dial-1-monoacetals are of great importance in terpene syntheses, since they make it possible to carry out successive Wittig reactions giving a very large number of compounds of biological and pharmacological importance.

6 Claims, No Drawings

PREPARATION OF CYCLIC ACETALS OF TRANS-4-CHLORO-3-METHYL-BUT-2-EN-1-AL, AND PREPARATION OF TRANS-3-METHYL-BUT-2-ENE-1,4-DIAL-1-MONOACETALS

The present invention relates to a process for the preparation of 6-membered cyclic acetals of trans-4-chloro-3-methyl-but-2-en-1-al by reacting the corresponding acetals of 3-methyl-but-2-en-1-al (prenal) with sulfuryl chloride, and to their subsequent oxidation to prepare the trans-3-methyl-but-2-ene-1,4-dial-1-monoacetals (3-methyl-fumarodialdehyde-1-monoacetals) which are useful for terpene syntheses.

The trans-3-methyl-but-2-ene-1,4-dial-1-monoacetals are of great importance since they may be used to carry out successive Wittig reactions to give a very large number of compounds of biological and pharmacological importance. For example, a simple method of obtaining the sought-after compound retinal is to react a trans-3-methyl-but-2-ene-1,4-dial-1-acetal with the ylide of a β-ionylideneethyltriphenylphosphonium salt, followed by hydrolysis. Retinal possesses the same activity as vitamin A. Furthermore, β-carotin can be prepared very economically by a simple Wittig reaction with the retinyltriphenylphosphonium salt which is easily obtainable from retinol.

Various processes for the preparation of trans-3-methyl-but-2-ene-1,4-dial-1-acetals have been disclosed. For example, German Laid-Open Application DOS No. 2,225,612 describes their preparation by oxidizing cyclic 3-methyl-but-2-en-4-ol-1-al-acetals with a chromic acid/sulfuric acid solution in acetone. This process gives relatively good yields. However, its industrial feasibility is made very difficult by the use of chromic acid as the oxidizing agent and by the severe effluent problems resulting from the toxicity of chromium compounds.

German Laid-Open Application DOS No. 2,357,752 discloses the preparation of the sought-after trans-3-methyl-but-2-ene-1,4-dial-1-acetals by oxidizing the corresponding 3-methyl-but-2-en-1-al-acetals with selenium oxide in certain solvents. The yields achieved with this process are unsatisfactory. Furthermore, the industrial operation of the process presents great problems because of the high toxicity of selenium.

Further, German Laid-Open Application DOS No. 2,513,999 discloses the preparation of trans-3-methyl-but-2-ene-1,4-dial-1-acetals, starting from crotonaldehyde-acetals, by ozonolysis followed by reductive working-up, Grignard vinylation, acetylation of the resulting glyoxal monoacetals, hydroformylation of the resulting novel 2-acetoxy-but-3-en-1-al-acetals and elimination of acetic acid. However, the numerous and in some cases troublesome steps involved in carrying out this process entail relatively high manufacturing costs.

It is an object of the present invention to provide a process whereby the sought-after trans-3-methyl-but-2-ene-1,4-dial-1-acetals can be prepared in a technically particularly simple manner, ie. with very low labor costs.

We have found that the readily accessible 6-membered cyclic acetals of 3-methyl-but-2-en-1-al (prenal) can, under quite specific conditions, be converted by means of sulfuryl chloride with high selectivity to the trans-4-chloro-3-methyl-but-2-en-1-al-acetals, and that these can, under mild oxidation conditions, be oxidized in good yields to the required trans-3-methyl-but-2-ene-1,4-dial-1-monoacetals.

Accordingly, the present invention relates to a process for the preparation of acetals of the general formula I

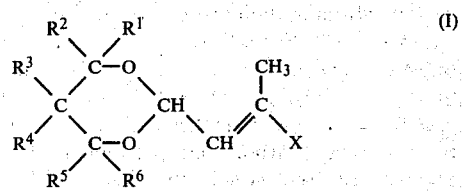

where $R^1$ to $R^6$ are —H, —CH$_3$ or —C$_2$H$_5$, preferably —H or —CH$_3$, but preferably only from 1 to 4 of the radicals $R^1$ to $R^6$ are —CH$_3$ and the remainder are —H, and X is —CH$_2$Cl or

wherein
(A) a molar amount, or slight excess, of sulfuryl chloride is introduced slowly into a solution of the corresponding acetal of 3-methyl-but-2-en-1-al of the formula II

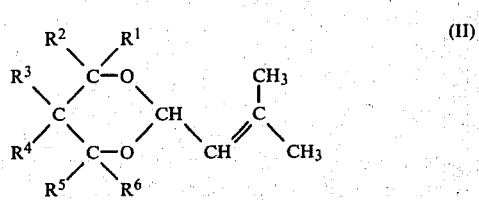

in a halohydrocarbon of boiling point 50°–120° C., at 50°–120° C., preferably at 80°–90° C., at the rate at which the sulfuryl chloride is consumed in the reaction mixture, and
(B) where X is

the resulting 4-chloro-3-methyl-but-2-en-1-al-acetal is oxidized under mild reaction conditions.

The process according to the invention proceeds in a particularly advantageous manner if, in reaction step A, the sulfuryl chloride is introduced into a boiling solution of the corresponding acetal of the formula II in trichloroethylene.

The best selectivity in respect of 4-chloro-3-methyl-but-2-en-1-al-acetals is obtained, in the process according to the invention, if in reaction step A about 1.1 moles of sulfuryl chloride per mole of acetal are introduced into the acetal solution in the course of from 1 to 2 hours.

The fact that the 6-membered cyclic acetals of 3-methyl-but-2-en-1-al can, under the conditions according to the invention, be converted with high selectivity to the sought-after 4-chloro-3-methyl-but-2-en-1-al-1- acetals is very surprising, for the reasons discussed below.

A review article in Houben-Weyl "Methoden der organischen Chemie", Volume 5/3, on the use of sulfuryl chloride as a chlorinating agent states, for example, that the addition of chlorine to unsaturated compounds by means of sulfuryl chloride occurs easily, with formation of saturated dichloro derivatives and $SO_2$ (cf. loc. cit., page 874). From this it would have been expected that the 3-methyl-but-2-en-1-al-acetals would, on reaction with $SO_2Cl_2$, substantially form 2,3-dichlorobutan-1-al-acetals, which indeed is the case, quantitatively, if hydrocarbons, eg. petroleum ether or cyclohexane, are used as solvents. Further, the article referred to states that sulfuryl chloride can produce 2 types of addition reactions; it can add 2 chlorine atoms to the olefinic double bond, or its entire molecule may react, to form chloroalkanesulfonic acid chlorides (cf. loc. cit., top of page 875). This statement, again, would not have led to an expectation of the reaction according to the invention. Further, the article referred to states that in a chlorination with sulfuryl chloride, as in a chlorination with elementary chlorine, secondary hydrogen reacts more easily than primary, and tertiary hydrogen reacts more easily than secondary (cf. loc. cit., page 877, paragraph 2). From this it would have been expected that the products would substantially have been 2-chloro-3-methyl-but-3-en-1-al-acetals.

It is also noteworthy that the chlorination with $SO_2Cl_2$ only succeeds with 6-membered cyclic acetals. If 5-membered cyclic acetals of prenal or of simple acetals, eg. dimethylacetal, are used, the acetals are destroyed by $SO_2Cl_2$. In attempts to use $Cl_2$ as a chlorinating agent, both the 5-membered cyclic acetals and the 6-membered cyclic acetals are destroyed.

It should also be mentioned that if tiglic aldehyde 6-membered cyclic acetals, ie. compounds which differ from the compounds of the formula II only in respect of the position of the methyl group, are reacted, exclusively the vicinal dichloride is formed even under the conditions according to the invention.

The acetals required as starting materials for the process according to the invention are obtained by acetalizing prenal with the 1,3-diols conforming to the definition. Prenal is a commercial product. It can be obtained, for example, by reacting isobutylene and formaldehyde, isomerizing the resulting 2-methyl-but-1-en-4-ol and then dehydrogenating the resulting 3-methyl-but-2-en-1-ol (cf. German Laid-Open Application DOS No. 2,041,976).

Examples of suitable starting materials are the acetals of 3-methyl-but-2-en-1-al with butane-1,3-diol, pentane-2,4-diol, propane-1,3-diol and, in particular, neopentyl glycol (2,2-dimethyl-propane-1,3-diol).

Sulfuryl chloride is a commercial compound.

Suitable solvents for the reaction according to the invention are halohydrocarbons which boil at from about 50° to 120° C. Examples include dichloroethylene, trichloroethylene, tetrachloroethylene, chloroform and chlorobenzene. The selectivity of the reaction is quite exceptionally high when trichloroethylene is used. With this solvent, the undesired by-products (2-chloro-3-methyl-but-2-en-1-al-acetals and 2,3-dichloro-3-methyl-butan-1-al-acetals) are produced in yields of only about 6% each, whilst if the other halohydrocarbons mentioned are used, the proportion of these by-products is higher.

Chlorination of the acetals II with $SO_2Cl_2$ without the use of a solvent does not succeed.

The amount of solvent used is in general from about 0.5 to 2 liters, preferably about 1 liter, per mole of starting acetal.

To carry out the chlorination according to the invention, the procedure followed is in general to dissolve the acetal in the solvent and slowly introduce the sulfuryl chloride into the resulting solution which has been heated to the temperature according to the invention, preferably into a refluxing solution. The $SO_2Cl_2$ cannot be introduced at a randomly chosen rate. The best results are achieved if about 1 mole of $SO_2Cl_2$ is introduced into a solution of 1 mole of the starting acetal in the course of from 1 to 2 hours. This means that the $SO_2Cl_2$ is introduced at about the rate at which it is consumed in the reaction mixture, ie. at which the chlorination proceeds.

According to the invention, the sulfuryl chloride is used in about equimolar amounts to the starting acetal, ie. in amounts of from about 1 mole to 1.2 moles per mole of acetal.

The reaction is in general carried out under atmospheric pressure.

The reaction mixture is worked up in a conventional manner by distilling off the solvent, with or without subsequent fractionation.

If the product is to be used for the preparation of trans-3-methyl-but-2-ene-1,4-dial-1-monoacetals, which are sought-after products for carotinoid synthesis, the crude material can be employed without additional purification, since, of the chlorides formed, only the 4-chloro derivative can be oxidized to the corresponding aldehyde.

If the trans-3-methyl-but-2-ene-1,4-dial-1-monoacetals are to be used directly for carrying out Wittig reactions, the solutions obtained from the oxidation, for example the solutions resulting from the oxidation with dimethylsulfoxide (DMSO), can be reacted direct, ie. without further purification, with phosphonium salts.

To prepare the sought-after trans-3-methyl-but-2-ene-1,4-dial-1-monoacetals, the chlorides of the formula I can be oxidized under mild reaction conditions.

An advantageous method for oxidizing the chlorides of the formula I under mild reaction conditions is, for example, to oxidize compound I with dimethylsulfoxide in the presence of a base, such as an alkali metal carbonate, alkali metal bicarbonate, alkaline earth metal carbonate or alkaline earth metal bicarbonate. The fact that this reaction can be carried out with good yields is surprising since Fieser and Fieser "Reagents for Organic Synthesis", John Wiley and Sons Inc., New York 1967, page 303, states that primary chlorides, on oxidation with dimethylsulfoxide, give only very poor yields and that therefore the chlorides must first be converted to the tosylates by means of silver tosylate (cf. also Tetrahedron Letters 11 (1974), 917 et seq.).

To oxidize a chloride of the formula I with dimethylsulfoxide, the procedure generally followed is to heat the chloride, or the chloride mixture obtained by chlorination with sulfuryl chloride according to process step A, in the presence of one or more of the above carbonates or bicarbonates, with not less than 1 mole of DMSO in an inert solvent, or with not less than 5 moles of DMSO in the absence of an inert solvent, at from about 50° to 150° C., preferably from 60° to 120° C. The reaction time is in general from about 0.5 to 2 hours, preferably from 1 to 1.5 hours. Examples of inert solvents which may be used are dimethylformamide and dimethylacetamide.

The reaction is advantageously carried out in excess dimethylsulfoxide. The amount of solvent used is advantageously from 5 to 100 times the amount by weight of the starting compound. If DMSO is used as the solvent, the total amount used is from 5 to 20, preferably from 5 to 10, moles per mole of chloride of the formula I.

The amount of base used is in general from 1 to 10 moles, preferably from 2 to 4 moles, per mole of chloride.

The oxidation of the chlorides of the formula I can however also be carried out with other conventional mild oxidizing agents. Examples include the sodium salts of aliphatic nitro compounds, eg. of 2-nitropropane and of nitrocyclohexane, amine oxides, eg. trimethylamine oxide and N-methyl-morpholine oxide, as well as hexamethylenetetramine in a Sommelet reaction.

The oxidation with a sodium salt of an aliphatic nitro compound may be carried out, for example, by reacting 1 mole of the allyl chloride of the formula I, 1 mole of the nitro compound and 1 mole of a sodium alcoholate or sodium hydroxide in a lower aliphatic alcohol or in a solvent such as dimethylformamide, at an elevated temperature. Since the chloromethyl group exhibits some steric hindrance, it is advisable to add a small amount of an auxiliary nucleophilic agent, eg. KI, to the reaction mixture. The reaction mixture is worked up in the conventional manner by pouring it into ice water, extracting and distilling.

The oxidation with amine oxides can be carried out, for example, by heating the allyl chloride I for several hours with the amine oxide in dimethylformamide, and then working up in a conventional manner.

The oxidation with hexamethylenetetramine is based on the fact that the allyl chlorides I undergo adduct formation with hexamethylenetetramine (in the molar ratio of 1:1) to form quaternary ammonium salts which, on heating with water, can easily be hydrolyzed to form the aldehyde I and methylamine, in addition to formaldehyde and ammonia. In this reaction it is not absolutely essential to prepare the quaternary compounds separately. For example, the allyl chloride I can be converted to the aldehyde of the formula I by heating with hexamethylenetetramine in dimethylformamide, to which a small amount of water has been added, as the solvent.

The oxidation of the chlorides of the formula I to the aldehydes of the formula I is described in Examples 2A to 2D.

Concerning further details of the conversion of chloromethyl groups to aldehyde groups, reference may be made to Methodicum Chimicum, Volume 5, Georg Thieme Verlag, Stuttgart 1975, pages 290–293, or Houben-Weyl, Methoden der Organischen Chemie, 4th Edition, Volume 7/1, pages 193–204.

Using the process according to the invention, the 6-membered cyclic acetals of trans-4-chloro-3-methyl-but-2-en-1-al and, from these, the trans-3-methyl-but-2-ene-1,4-dial-1-monoacetals sought-after for carotinoid syntheses, can be prepared in a simple manner and in good yields.

EXAMPLE 1

17 kg (100 moles) of 3-methyl-but-2-en-1-al-(2',2'-dimethyl-propylene)-acetal were dissolved in 120 liters of trichloroethylene and the solution was heated to the boil. 9 liters (111 moles) of sulfuryl chloride were added, over 90 minutes, to the solution refluxing at 87° C., and the reaction mixture was then kept at the boil for a further hour. After the reaction mixture had cooled to 20° C., 50 liters of water and 10 kg of Na$_2$CO$_3$ were added, the batch was stirred, the phases were then separated, and the organic phase was concentrated. Examination by gas chromatography showed that the starting material had been completely converted. The yield of 4-chloro-3-methyl-but-2-en-1-al-(2',2'-dimethyl-propylene)-acetal was 85%, accompanied by 6% of the corresponding 2-chloro-3-methyl-but-3-en-1-al-acetal and 6% of the corresponding 2,3-dichloro-butan-1-al-acetal. Working up by distillation gave 15.6 kg, corresponding to 76% yield, of the 4-chloroacetal.

EXAMPLE 2

A. Oxidation with DMSO/Na$_2$CO$_3$ 20 g of the mixture obtained as described in Example 1 were dissolved in 80 g of dimethylsulfoxide (DMSO), 20 g of finely powdered Na$_2$CO$_3$ were added to the solution and the mixture was heated at 120° C., whilst stirring. After a reaction time of 2½ hours, 98% of the 4-chloro-3-methyl-but-2-en-1-al-(2',2'-dimethyl-propylene)-acetal had been converted. The acetals of 2-chloro-3-methyl-but-3-en-1-al and 2,3-dichloro-butan-1-al, present in the mixture, remained unaffected. Examination of the reaction solution by gas chromatography indicated a yield of trans-3-methyl-but-2-ene-1,4-dial-1-(2',2'-dimethyl-propylene)-acetal of 73%, based on chloride converted.

The reaction mixture was worked up by pouring it into water, extracting the product with ether and subjecting it to fractional distillation. Yield 67%. If used for a Wittig reaction, the trans-3-methyl-but-2-ene-1,4-dial-1-(2',2'-dimethyl-propylene)-acetal obtained can, however, also be used directly as the DMSO solution, without additional purification, for reaction with a phosphonium salt.

B. Oxidation with 2-nitropropane 10 g of the distilled allyl chloride obtained as described in Example 1, 6 ml of 2-nitropropane and 1 g of KI were jointly dissolved in 80 ml of dimethylformamide (DMF). The solution was heated at 40° C. and 4.8 g of a 50% strength sodium hydroxide solution were added dropwise over 60 minutes. The reaction mixture was then cooled to 20° C., left to stand for an hour whilst being stirred, and then poured onto an ice/water mixture. Extraction with toluene, and subsequent distillation of the extract, gave 6.2 g (corresponding to 69% of theory) of trans-3-methyl-but-2-ene-1,4-dial-1-(2',2'-dimethyl-propylene)-acetal of boiling point 71° C./0.1 mbar.

C. Oxidation with trimethylamine oxide 10 g of the distilled allyl chloride obtained as described in Example 1 and 7 g of anhydrous trimethylamine oxide were jointly dissolved in 60 ml of dimethylformamide. The solution was stirred for 3 hours at 60° C. and then cooled and poured into water. Subsequent extraction with toluene, and distillation of the crude product, gave 6.4 g (corresponding to 71% of theory) of trans-3-methyl-but-2-ene-1,4-dial-1-(2',2'-dimethyl-propylene)-acetal.

D. Oxidation with hexamethylenetetramine (Sommelet reaction)

10 g of the distilled allyl chloride obtained as described in Example 1, 10 g of urotropine (hexamethylenetetramine) and 1 g of KI were dissolved in a mixture of 100 ml of DMF and 5 ml of water. The solution was heated for 1 hour at 80° C. and then cooled and worked up as described in B. 4.9 g (corresponding to 54% of theory) of trans-3-methyl-but-2-ene-dialdehyde-1-(2',2'-dimethyl-propylene)-acetal were obtained.

EXAMPLE 3

17 g (0.1 mole) of 3-methyl-but-2-en-1-al-(2',2'-dimethyl-propylene)-acetal were dissolved in 100 ml of trichloroethylene, and 14.8 g (0.11 mole) of SO$_2$Cl$_2$ were then added over 1 hour, at one of the temperatures shown in the Table below. The various yields of 4-chloro-3-methyl-but-2-en-1-al-(2',2'-dimethyl-propylene)-acetal (A), 2-chloro-3-methyl-but-3-en-1-al-(2',2'-dimethyl-propylene)-acetal (B) and 2,3-dichloro-butan-1-al-(2',2'-dimethyl-propylene)-acetal (C) obtained are listed in the Table.

|  |  | Yield |  |  |
|---|---|---|---|---|
| Solvent | Temperature | % A | % B | % C |
| Trichloroethylene | 0° C. | 0 | 0 | 100 |
| " | 60° C. | 35 | 25 | 35 |
| " | 87° C. (reflux under atmospheric pressure) | 85 | 6 | 6 |

EXAMPLES 4 TO 7 AND COMPARATIVE EXAMPLES 8 TO 11

17 g (0.1 mole) portions of 3-methyl-but-2-en-1-al-(2',2'-dimethyl-propylene)-acetal were dissolved in 100 ml of each of the solvents shown in the Table, and the solution was heated to the boil. 14.8 g (0.11 mole) of SO$_2$Cl$_2$ were added over 1 hour to the refluxing solution. The respective yields of A, B and C (the symbols being defined in Example 3) are listed in the Table which follows.

|  |  | Yield |  |  |
|---|---|---|---|---|
| Example | Solvent | % A | % B | % C |
| 4 | CHCl$_3$ | 43 | 37 | 0 |
| 5 | C$_2$Cl$_4$ | 65 | 20 | 0 |
| 6 |  | 72 | 22 | 0 |
| 7 | CH$_2$Cl$_2$ | 41 | 34 | 14 |
| 8 | C$_7$H$_{16}$ | 33 | 23 | 28 |
| 9 | Petroleum ether, boiling point 60° C. | 0 | 0 | 100 |
| 10 | Cyclohexane | 0 | 0 | 100 |
| 11 | Petroleum ether, boiling point 90° C. | 0 | 0 | 100 |

We claim:

1. A process for the preparation of an acetal of the general formula I

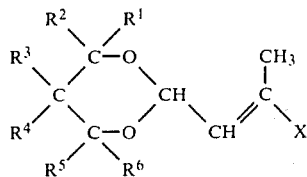

wherein R$^1$ to R$^6$ are independently —H, —CH$_3$ or —C$_2$H$_5$ and X is —CH$_2$Cl or

wherein (A) a molar amount or slight excess of sulfuryl chloride is introduced slowly into a solution of the corresponding acetal of 3-methyl-but-2-en-1-al of the formula II

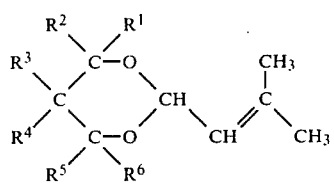

in a halohydrocarbon of boiling point 50°–120° C., at 50°–120° C., at the rate at which the sulfuryl chloride is consumed in the reaction mixture, and (B) where X is

the resulting 4-chloro-3-methyl-but-2-en-1-al-acetal is oxidized under mild reaction conditions.

2. A process as claimed in claim 1, wherein, in step A, the sulfuryl chloride is introduced into a boiling solution of the corresponding acetal of the formula II in trichloroethylene.

3. A process as claimed in claim 1, wherein, in step A, about 1.1 moles of sulfuryl chloride are introduced, in the course of from 1 to 2 hours, into a solution of about 1 mole of the acetal II.

4. A process as claimed in claim 1, wherein, in step B, 4-chloro-3-methyl-but-2-en-1-al-acetal is oxidized with dimethylsulfoxide in the presence of an alkali metal carbonate, alkali metal bicarbonate, alkaline earth metal carbonate or alkaline earth metal bicarbonate.

5. A process as claimed in claim 1, wherein R$^1$ to R$^6$ are independently —H or —CH$_3$.

6. A process as claimed in claim 5, wherein 1 to 4 of the radicals R$^1$ to R$^6$ are —CH$_3$ and the remainder are —H.

* * * * *